(12) United States Patent
Muscate-Magnussen et al.

(10) Patent No.: US 6,379,515 B1
(45) Date of Patent: Apr. 30, 2002

(54) PROCESS FOR SEPARATING MIXTURES OF SUBSTANCES USING CAPILLARY AFFINITY GEL ELECTROPHORESIS

(75) Inventors: Angelika Muscate-Magnussen, Hamburg (DE); Aran Paulus, Fremont, CA (US); François Natt, Aesch (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/180,984

(22) PCT Filed: May 23, 1997

(86) PCT No.: PCT/EP97/02647

§ 371 Date: Nov. 19, 1998

§ 102(e) Date: Nov. 19, 1998

(87) PCT Pub. No.: WO97/45721

PCT Pub. Date: Dec. 4, 1997

(30) Foreign Application Priority Data

May 24, 1996 (CH) .............................................. 1320/96

(51) Int. Cl.$^7$ ....................... G01N 27/26; G01N 27/447
(52) U.S. Cl. ........................ 204/451; 204/455; 204/601; 204/605
(58) Field of Search .............................. 204/455, 454, 204/453, 452, 451, 469, 456, 605, 604, 603, 602, 601

(56) References Cited

U.S. PATENT DOCUMENTS

5,126,021 A    6/1992  Grossman .................. 204/180.1
5,348,658 A  * 9/1994  Fuchs et al. ................ 210/656

FOREIGN PATENT DOCUMENTS

| EP | 0 442 177 A  | 8/1991  |
| EP | 0 459 241 A  | 12/1991 |
| EP | 0 500 211 A  | 8/1992  |
| EP | 0 534 017 A  | 3/1993  |
| EP | 0 671 626 A1 | 9/1995  |
| WO | 95/10344     | 4/1995  |

OTHER PUBLICATIONS

Steven Ostrove, "Affinity Chromatography: General Methods" Methods in Enzymology, vol. 82 (1990) 357–379.*
Harry W. Jarrett, "Affinity chromatography with nucleic acid polymers" Journal of Chromatography, vol. 618 (1993) 315–339.*
Yoshinobu Baba, "Capillary Affinity Gel Electrophoresis" Molecular Biotechnology, vol. 6 (1996) 143–153.*
Baba et al., "Temperature–programmed capillary affinity gel electrophoresis for the sensitive base–specific separation of oliogodeoxynucleotides", Journal of Chromatography, vol. 632, pp. 137–142, 1993.
Birnbaum et al., "Protein–Based Capillary Affinity Gel Electrophoresis for the Separation of Optical Isomers", Analytical Chemistry, vol. 64, pp. 2872–2874, 1992.
Goubran–Botros et al., "Immobilized metal ion affinity electrophoresis, A study with several model proteins containing histidine", Journal of Chromatography, vol. 597, pp. 357–364, 1992.
Horejsi et al., "Affinity Electrophoresis: New Simple and General Methods of Preparation of Affinity Gels", Analytical Biochemistry, vol. 125, pp. 358–369, 1982.
Igloi, Gabor L., "Interaction of tRNAs and of Phosphorothioate–Substituted Nucleic Acids with an Organomercurial. Probing the Chemical Environment of Thiolated Residues by Affinity Electrophoresis", Biochemistry, vol. 27, pp. 3842–3849, 1988.
Jarrett, Harry W., "Affinity chromatography with nucleic acid polymers", Journal of Chromatography, vol. 618, pp. 315–339, 1993.
Ostrove, Steven, "Affinity Chromatography: General Methods", Methods in Enzymology, vol. 82, pp. 357–379, 1990.
Paulus et al., "Analysis of oligonucleotides by capillary gel electrophoresis", Journal of Chromatography, vol. 507, pp. 113–123, 1990.
Sun et al., "Chiral separations using an immobilized protein—dextran polymer network in affinity capillary electrophoresis", Journal of Chromatography A, vol. 652, pp. 247–252, 1993.

* cited by examiner

*Primary Examiner*—Jill Warden
*Assistant Examiner*—John S. Starsiak, Jr.
(74) *Attorney, Agent, or Firm*—Perkins Coie LLP

(57) ABSTRACT

Process for the selective separation of electrically charged target molecules in an analytical mixture by means of capillary affinity gel electrophoresis, using a capillary tube which is at least partly filled with a polymer gel, whereby receptors for target molecules are covalently bound to the polymer, and an electric field of at least 50 volts/cm is applied, characterized in that (a) the capillary tube is charged with the analytical mixture, (b) in a first separation stage the target molecules in the analytical mixture are bound to the receptors and the remaining components are eluted, optionally while splitting open, and (c) in a second stage of the process the elution conditions are changed, optionally in stages, so that the affinity of the target molecules for the receptor is eliminated and the target molecules are eluted and detected, optionally whilst splitting open.

7 Claims, No Drawings

PROCESS FOR SEPARATING MIXTURES OF SUBSTANCES USING CAPILLARY AFFINITY GEL ELECTROPHORESIS

The present invention relates to a process in stages for the selective separation and/or determination of charged organic compounds. In this process, mixtures containing these organic compounds are subjected to conditions of high binding affinity of capillary affinity gel electrophoresis, whereby the capillary tube is filled with a gel based on polymers as the separating agent, to which the specific recognition elements (receptors) for one or several organic compounds are covalently bound. By applying an electric field, the undesired portions of the mixture of substances are separated optionally whilst splitting them open, and then the affinity conditions are changed, so that the bound compounds are eluted and detected, optionally whilst splitting them open. Further objects of the invention are the separating agents which may be filled into the capillary tubes for the capillary affinity gel electrophoresis and their usage for the separation of charged organic compounds.

Column-chromatography processes have acquired great importance and found a wide application for the preparatory separation and purification of, in particular, biologically active compounds. Of the liquid chromatography processes, gel chromatography with polymeric gels as separating agents, or the stationary phase, is particularly widespread. Since, in many cases, this method does not satisfy requirements, improvements are always being proposed. Some time ago, it was proposed that specific receptors, for example oligonucleotides or proteins, should be bound to the polymeric gels, and that owing to their interaction and affinity, they would bind to biological molecules, the molecules would be retained under certain conditions of elution and allow the undesired secondary components to be separated. With the change in elution conditions, the affinity may be influenced so that it is possible to elute the desired, purified compound. This method of affinity chromatography has been described for example by H. W. Jarrett in the Journal of Chromatography, Biomedical Applications, 618 (1993), pages 315 to 31, or by S. Ostrove in Methods of Enzymologie, volume 182 (1990), pages 357 to 379.

Another known method for the preparatory separation is the gel electrophoresis process for separating charged compounds, which is used in particular in the biochemical field for the separation of peptides, antigens, antibodies and oligo- to polynucleotides. Normally, plates or rods of the gel are used with the covalently bound receptors, as described for example in DE-A-2 712 344, by V. Horejsi in Analytical Biochemistry 125, pages 358 to 369 (1982) and in the Journal of Chromatography, 376 (1986), pages 49 to 67, by G. L. Igloi in Biochemistry 27 (1988), pages 3842 to 3849, and by H. Goubran-Botros et al. in the Journal of Chromatography, 597 (1992), pages 357 to 364. This method may also be set up as a column process, see for example FR-A-2 402 716, the description of which discloses the continuous elution and concentration of a the testerone antibody with the assistance of a polymer-bound antigen at a pH of just below the isoelectric point of the antibody.

For analytical separation and determination processes of charged organic compounds, the capillary gel electrophoresis method is more suitable, since on the one hand one can use smaller amounts of samples, this method is considerably more sensitive and high resolutions may be attained. Also, this method is faster to carry out and can even be operated automatically. An example which may be mentioned is the analytical separation of oligonucleotides, as described by A. Paulus et al. in the Journal of Chromatography, 507 (1990), pages 113 to 123.

Proposals have also already been disclosed, which link capillary gel electrophoresis with affinity chromatography. In WO 95/10344, polymer globules with covalently bound receptors are bound chemically to the inside wall of a capillary tube. In this way, in a continuous elution process, the separation output ought to be improved. However, the number of covalently bound receptors is very small and restricted, due to the specific construction, so that the sensitivity is often unsatisfactory. Furthermore, the chemical binding of the separation material to the inside wall of the capillary tube is very complicated and restricts its application.

In the Journal of Chromatography 632 (1993), pages 137 to 142, Y. Baba et al. describe a continuous process for the separation of oligodesoxynucleotides by means of capillary affinity gel electrophoresis. By using polyvinyl adenine as the stationary phase, selectivity ought to be improved. However, this aim cannot be completely attained, since although certain interactions between the analytical substance and the receptor do take place, no fixed bindings arise as when using complementary receptors. Therefore, the selectivity is wholly unsatisfactory for many purposes, especially for separating oligonucleotide mixtures, the continuous elution also making a substantial contribution to this.

In Anal. Chem. 64 (1992), pages 2872 to 2874, S. Birnbaum et al. describe the separation of optical isomers of tryptophan by continuous elution using capillary affinity gel electrophoresis, whereby the chiral selector employed is a BSA gel (BSA=bovine serum albumin) which is crosslinked with glutaraldehyde. However, the separation and detection of analytical mixtures using such gels as separating agents is not possible, since specific targeted bindings to receptors are not possible.

In EP-A-0 671 626, capillary tubes are described for capillary affinity gel electrophoresis, in which receptors are bound to the inside wall of a first part of the capillary tube and the remainder of the capillary tube is filled with a buffer. In the separation process, for example, a mixture of labelled and unlabelled analytical molecules may be bound to the receptors and the unbound portions eluted. Afterwards, the elution conditions are changed (pH change, addition of organic solvent, other buffers) and the labelled and unlabelled analytical molecules are dissolved and then separated in the subsequent gel. In this construction also, due to the specific set-up, the number of covalently bound receptors is too small to obtain separations with high sensitivity. In addition, production of the capillary tubes is complicated and the chemical possibilities of binding to receptors are greatly restricted by the material of the capillary tubes and the functional groups present.

In the Journal of Chromatography A 652 (1993), pages 247 to 252, P. Sun et al. describe the covalent binding of BSA to a high molecular weight dextran ($M_r$ 2,000,000). The immobilised polymer is used as a replaceable chiral separating agent for the enantiomers of leucovorin in capillary affinity gel electrophoresis, whereby a continuous procedure is similarly employed. In this process also, the selectivity and sensitivity leave a lot to be desired; in particular, the selective separation and detection of target analytical substances, as well as other analytical components, with high selectivity and sensitivity, is not possible with the process described.

It has now surprisingly been found that target molecules even in capillary affinity gel electrophoresis may be retained completely by selecting certain conditions, and eluted completely by changing the conditions, when using as separating agent polymer gels with covalently bound receptors complementary to target analytical substances. It was also surprisingly found that the analytical substances and mixtures of analytical substances may be separated and detected (1) with very high selectivity and sensitivity, as well as (2) rapidly and specifically, and (3) other components of the analytical substance may be simultaneously separated and determined, and (4) furthermore separations of this type may be carried out in fully-automatic on-line apparatus, if in the capillary affinity gel electrophoresis (a) a polymer gel is used as the separating agent, the gel containing receptors which are complementary to one or several of the target molecules to be separated and are covalently bound either directly or by a bridging group to the spine of the polymer, and (b) elution is carried out in two stages or many stages by changing the elution conditions.

One object of the invention is a process for the selective separation of electrically charged target molecules in an analytical mixture by means of capillary affinity gel electrophoresis, using a capillary tube which is at least partly filled with a polymer gel which is solid, or a solution of the polymer in a solvent, having a viscosity of at least 20 mPa·s, whereby receptors for target molecules are covalently bound to the polymer, and an electric field of at least 50 volt/cm is applied, which process is characterised in that (a) the capillary tube is loaded with the analytical mixture, (b) in a first separation stage the target molecules in the analytical mixture are bound to the receptors and the remaining components are eluted, and (c) in a second stage of the process the elution conditions are changed, optionally in stages, so that the affinity of the target molecules for the receptor is suspended and the target molecules are eluted and detected.

Within the scope of the invention, receptor signifies an organic molecule which is complementary to a target molecule, so that under given conditions it is bound by its steric arrangement and/or secondary valence bonds (for example hydrogen bridges), electrostatic forces or hydrophobic effects, and/or Van der Waals forces.

Within the scope of the invention, polymer gel signifies that either a solid gel exists, or a solution of the polymer in a solvent has a viscosity of at least 20 mPa·s. The viscosity is determined basically by the properties (molecular weight) and the concentration of the polymer in the solution.

The same or different receptors may be bound to the polymer. If different receptors are bound, there may be up to 10, preferably up to 5, most preferably up to 3 different receptors.

Polymer gels with covalently bound receptors (hereinafter called immobilised polymers), and their production, are known in large number from affinity gel chromatography, or they may be produced by analogous processes. In capillary gel electrophoresis, polymers are conveniently employed, which have average molecular weights of 5000 to 5,000,000, more preferably 10,000 to 2,000,000, even more preferably 10,000 to 1,000,000 and most preferably 20,000 to 500,000 daltons. The molecular weights are determined by gel permeation chromatography with the assistance of polymers of known molecular weights as a standard.

The polymers must contain function groups, to which the functionalised receptors may be bound, Gel-forming polymers are soluble or capable of swelling in water, solvents or mixtures of water (buffer) and solvents, particularly if they are crosslinked polymers. It is very appropriate here to adjust the viscosities of the solutions so that it is possible to fill the capillary tube and to replace the content. A large number of suitable water-soluble polymers are known. The choice of polymer and its molecular weight, as well as its concentration in the composition, determine the viscosity. The required molecular weight may be obtained either by means of specific synthesis, by dialysis or by a for example hydrolytic degradation of higher molecular weight polymers. The polymers must be stable under the chosen separation conditions. Both synthetic and natural polymers may be used. Examples are optionally partly etherified or esterified polyvinyl alcohols, polyvinyl pyrrolidone, optionally N-monoalkylated polyacrylamides or -methacrylamides, polyhydroxyalkyl acrylates and methacrylates, polyethylene glycols or copolymers of ethylene glycol and 1,2-diols, for example 1,2-propylene glycol, polysaccharides or derivatives of polysaccharides, for example cellulose and cellulose ether, starch, dextrans and carragenan. Dendrimers are also suitable as polymers. Slightly crosslinked polymers may also be used, or the polymers may be crosslinked after filling the capillary tubes. Furthermore, it is possible to fill solutions of the monomers into the capillary tubes and to carry out polymerisation afterwards. The receptors are bound to the spine of the polymer either directly or through a bridging group. Also, such receptors may be bound to the functional terminal groups of a polymer, for example to the hydroxyl group of a polyethylene glycol. The immobilised polymers may be homopolymers or copolymers, which contain the structural elements with covalently bound receptors in a quantity of 0.01 to 99.9, preferably 0.1 to 90, more preferably 0.1 to 60, even more preferably 0.1 to 40, and most preferably 0.1 to 30 % by weight, based on the monomers. It is most preferable to use copolymers, especially those which contain 0.1 to 10, most preferably 0.1 to 5 % by weight of structural elements with covalently bound receptors.

Preferred water-soluble polymers are polyethylene glycols, polyacryl- or -methacryl-amides, polyhydroxyalkyl acrylates and methacrylates, and polyvinyl alcohols. The polyacryl- or -meth-acryl-amides are preferred in particular.

The receptor may be bound to the spine of the polymer either directly or by a bridging group, whereby the bridging group variant is preferred.

The bridging group may contain 1 to 60 atoms, preferably 5 to 60 atoms, more preferably 5 to 50 atoms, and most preferably 10 to 40 atoms, selected from the group C, O, S, P and N. The bridging group is preferably made up of hydrocarbon radicals which may be interrupted by one or several hetero atoms from the group O, S and N and/or the group —C(=O)—.

The radical of a receptor bound to the polymer spine may correspond for example to formula I,

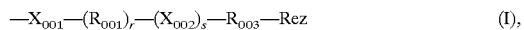

$$—X_{001}—(R_{001})_r—(X_{002})_s—R_{003}—Rez \quad (I),$$

wherein $X_{001}$ signifies a direct bond, or $X_{002}$ and $X_{001}$ independently of one another signify —O—, —S—, —NR$_{002}$—, —C(O)—O—, —O—C(O)—, —O—C(O)—O—, —SO$_2$—O—, —O—SO$_2$—, —O—SO$_2$—O—, —NR$_{002}$—C(O)—, —C(O)—NR$_{002}$—, —NR$_{002}$—C(O)—O—, O—C(O)—NR$_{002}$—, NR$_{002}$—C(O)—NR$_{002}$—, —NR$_{002}$—SO$_2$—, —SO$_2$—NR$_{002}$—, —NR$_{002}$SO$_2$—O—, —O—SO$_2$—NR$_{002}$—, —NR$_{002}$—SO$_2$—NR$_{002}$—, —O—P(O)OR$_{12}$(O)—, —NR$_{002}$—P(O)OR$_{12}$(O)—, —O—P(O)O R$_{12}$—NR$_{002}$—, —NR$_{002}$—P(O)O R$_{12}$—NR$_{002}$—, —P(O)O R$_{12}$—(O)— or —P(O)OR$_{12}$—NR$_{002}$—, $R_{001}$ represents a bivalent bridging group, Rez denotes a monovalent radical of a receptor, $R_{002}$ signifies H, $C_1$–$C_{12}$-alkyl, $C_5$- or $C_6$-cycloalkyl, C5- or $C_6$-cycloalkylmethyl or -ethyl, phenyl, benzyl or 1-phenyleth-2-yl, $R_{003}$ signifies a direct bond, $C_1$–$C_{18}$-alkylene, $C_5$- or $C_6$-cycloalkylene, $C_6$–$C_{10}$-arylene or $C_7$–$C_{12}$-aralkylene, $R_{12}$ denotes H, $C_1$–$C_{12}$-alkyl, ammonium, an alkali metal ion, for example $Li^+$, $Na^+$ and $K^+$, or an equivalent or an alkaline earth metal ion, for example $Mg^{2+}$ and $Ca^{2+}$;

r signifies the numbers 0 or 1, and s signifies the numbers 0 or 1, and s is 0 when r is 0.

The ammonium in question may be $NH_4^+$ or the ammonium may be derived from primary, secondary, tertiary amines or quaternary ammonium, which preferably contain 1 to 20 C-atoms.

$R_{002}$ when defined as alkyl preferably contains 1 to 6 and most preferably 1 to 4 C-atoms. A few examples are methyl, ethyl, n- or i-propyl, butyl, hexyl and octyl. $R_{002}$ when defined as cycloalkyl is preferably cyclohexyl, and when defined as cycloalkylmethyl is cyclohexylmethyl. In a preferred embodiment, $R_{002}$ represents H or $C_1$–$C_4$-alkyl.

The bivalent bridging group preferably represents a hydrocarbon radical, which preferably contains 1 to 30, more preferably 1 to 20, most preferably 1 to 16, especially 1 to 12 C-atoms, and which is unsubstituted or substituted once or several times by $C_1$–$C_4$-alkyl, $C_1$–$C_4$-alkoxy or =O. The hydrocarbon radical may also be interrupted once or several times by hetero atoms selected from the group —O—, —S— and —$NR_{002}$—, whereby $R_{002}$ preferably represents H or $C_1$–$C_4$-alkyl.

The bivalent bridging group in question may be for example $C_1$–$C_{20}$-, preferably $C_2$–$C_{12}$-alkylene, which may be linear or branched. A few examples are methylene, ethylene, 1,2- or 1,3-propylene, 1,2-, 1,3- or 1,4-butylene, pentylene, hexylene, octylene, dodecylene, tetradecylene, hexadecylene and octadecylene.

The bivalent bridging group in question may be for example polyoxa-alkylene with 2 to 12, preferably 2 to 6, most preferably 2 to 4 oxa-alkylene units and 2 to 4, preferably 2 or 3 C-atoms in the alkylene. It is most preferably polyoxa-ethylene and polyoxa-propylene with 2 to 6 oxa-alkylene units.

The bivalent bridging group in question may be for example $C_5$–$C_{12}$-, preferably $C_5$–$C_8$-, and most preferably $C_5$- or $C_6$-cycloalkyl, for example cyclopentylene, cyclohexylene, cyclooctylene or cyclododecylene.

The bivalent bridging group in question may be for example $C_5$–$C_{12}$-, preferably $C_5$–$C_8$-, and most preferably $C_5$- or $C_6$-cycloalkyl-$C_1$–$C_{12}$- and preferably -$C_1$–$C_4$-alkyl. A few examples are cyclopentyl-$C_nH_{2n}$— and cyclohexyl-$C_nH_{2n}$—, wherein n denotes a number from 1 to 4. Cyclohexyl-$CH_2$— is preferred in particular.

The bivalent bridging group in question may be for example $C_5$–$C_{12}$-, preferably $C_5$–$C_8$-, and most preferably $C_5$- or $C_6$-cycloalkyl-($C_1$–$C_{12}$-alkyl)$_2$- and preferably (—$C_1$–$C_4$-alkyl)$_2$. A few examples are cyclopentyl-($C_nH_{2n}$—)$_2$ and cyclohexyl-($C_nH_{2n}$—)$_2$, wherein n denotes a number from 1 to 4. —$CH_2$-cyclohexyl-$CH_2$— is preferred in particular.

The bivalent bridging group in question may be for example $C_6$–$C_{14}$-arylene and preferably $C_6$–$C_{10}$-arylene, for example naphthylene or more preferably phenylene.

The bivalent bridging group in question may be for example $C_7$–$C_{20}$-aralkylene and preferably $C_7$–$C_{12}$-aralkylene. More preferred is arylene-$C_nH_{2n}$—, wherein arylene denotes naphthylene and especially phenylene and n denotes a number from 1 to 4. Examples are benzylene and phenylethylene.

The bivalent bridging group in question may be for example arylene-($C_nH_{2n}$—)$_2$—, wherein arylene is preferably naphthylene and especially phenylene, and n denotes a number from 1 to 4. Examples are xylylene and phenylene ($CH_2CH_2$)$_2$—.

$R_{003}$ as alkylene preferably contains 1 to 12 and most preferably 1 to 6 C-atoms. Especially preferred examples are methylene, ethylene, 1,2- or 1,3-propylene and 1,2-, 1,3- and 1,4-butylene. $R_3$ as arylene is preferably phenylene and as aralkylene is preferably benzylene.

$R_{12}$ as alkyl preferably contains 1 to 8, and most preferably 1 to 4 C-atoms. Examples of alkyl are methyl, ethyl, propyl, butyl, pentyl, hexyl, heptyl and octyl.

In a preferred embodiment, the radical of formula I corresponds to formula Ia,

$$—X_{003}—R_{005}—Y—X_{004}—Rez \qquad (Ia),$$

wherein $X_{003}$ signifies a direct bond or —O—, —S—, —$NR_{002}$—, —C(O)—O—, —O—C(O)—, —O—C(O)—O—, —$SO_2$—O—, —O—$SO_2$—, —O—$SO_2$—O—, —$NR_{002}$—C(O)—, —C(O)—$NR_{002}$—, —$NR_{002}$—C(O)—O—, O—C(O)—$NR_{002}$—, $NR_{002}$—C(O)—$NR_{002}$—, —$NR_{002}$—$SO_2$—, —$SO_2$—$NR_{002}$—, —$NR_{002}SO_2$—O—, —O—$SO_2$—$NR_{002}$—, —$NR_{002}$—$SO_2$—$NR_{002}$—, —O—P(O)O$R_{12}$($O^-$)—, —$NR_{002}$—P(O)O$R_{12}$—(O)—, —O—P(O)O$R_{12}$—$NR_{002}$—, —$NR_{002}$—P(O)O$R_{12}$—$NR_{002}$—, —P(O)O$R_{12}$(O)— or —P(O)O$R_{12}$—$NR_{002}$—;

$X_{004}$ signifies a direct bond or —O—, —S— or —$NR_{002}$ with $R_{002}$ the same as H or signifies $C_1$–$C_4$-Alkyl, $R_{005}$ signifies $C_1$–$C_{20}$-alkylene, or $C_2$–$C_{18}$-alkylene which is interrupted once or several times by —O—, —S—, —O—C(O)—, —C(O)—O—, —$NR_{002}$—C(O)—, —C(O)—$NR_{002}$—, —O—C(O)—O—, —O—C(O)—$NR_{002}$—, —$NR_{002}$—C(O)—O—, —$NR_{002}$—C(O)—, —O—P(O)O$R_{12}$($O^-$)—, —$NR_{002}$—P(O)O$R_{12}$—(O)—, —O—P(O)O$R_{12}$—$NR_{002}$—, —$NR_{002}$—;

Y signifies a direct bond or represents —O—C(O)—, —$NR_{002}$—C(O)—, —O—P(O)(O$R_{12}$)O— or —$NR_{002}$—P(O)—O—, $R_{002}$ denotes H or $C_1$–$C_4$-alkyl, $R_{12}$ denotes H, $C_1$–$C_{12}$-alkyl, ammonium, an alkali metal ion, for example $Li^+$, $Na^+$ and $K^+$, or an equivalent of an alkaline earth metal ion, for example $Mg^{2+}$ and $Ca^{2+}$; and Rez signifies the radical of a receptor.

Radicals of receptors, especially biospecific receptors, which are complementary to target analytical substances, are known in large number. The radicals may be derived for example from antigens or fragments thereof, antibodies or fragments thereof, hormones, proteins (for example enzymes) or fragments thereof, RNA and DNA molecules or fragments thereof, natural or synthetic oligonucleotides, carbohydrates or fragments thereof, peptides or fragments thereof and natural or synthetic, biological active ingredients.

In a preferred sub-group of polymers to be used according to the invention, the polymers in question may be for example those which contain the same or different recurring structural elements of formula II, or the same or different structural elements of formulae II, and III,

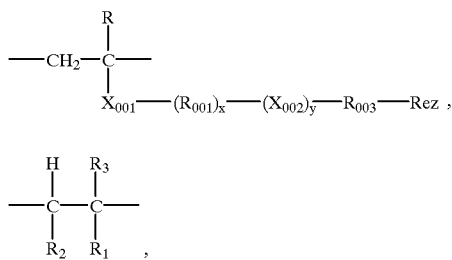

(II)

(III)

wherein $X_{001}$, $R_{001}$, $X_{002}$, $R_{003}$ and Rez have the significances given above for formula I;

R denotes H or $C_1$–$C_4$-alkyl;

$R_3$ signifies H, $C_1$–$C_{10}$-alkyl, phenyl or $C_1$–$C_4$-alkylphenyl;

$R_2$ represents H, —C(O)—$OR_4$ or —C(O)—$NR_5R_6$;

$R_1$ represents H, Cl, —CN, —OH, —$OC_1$–$C_6$-alkyl, —O—(O)C—$R_8$, —$OC_1$–$C_6$-hydroxyalkyl, phenyl, $C_1$–$C_4$-alkylphenyl, —C(O)—$OR_4$ or —C(O)—$NR_5R_6$, or $R_1$ and $R_2$ together signify —O—$C_1$–$C_{12}$-alkylidene—O—;

$R_4$ signifies H, ammonium, an alkali metal ion, an equivalent alkaline earth metal ion, $C_1$–$C_{12}$-alkyl, phenyl or $C_1$–$C_4$-alkylphenyl;

$R_5$ and $R_6$, independently of one another, denote H, $C_1$–$C_{12}$-alkyl, $C_1$–$C_8$-hydroxyalkyl, cyclohexyl, benzyl or phenyl, or $R_5$ and $R_6$ together denote tetra- or pentamethylene, —$(CH_2)_2$—O—$(CH_2)_2$— or —$(CH_2)_2$—$NR_7$—$(CH_2)_2$—, whereby $R_7$ is H or $C_1$–$C_4$-alkyl, x und y each denote 0 or 1 and x+y are 1 or 2; and $R_8$ signifies $C_1$–$C_{12}$-alkyl, $C_1$–$C_4$-halogenalkyl, $C_5$- or $C_6$-cycloalkyl, benzyl or phenyl.

For $X_{001}$, $R_{001}$, $X_{002}$, $R_{003}$, $R_{12}$ and Rez, the above-mentioned preferred significances and amplifications are applicable.

R preferably signifies H or methyl.

$R_3$ as alkyl preferably denotes $C_1$–$C_4$-alkyl. $R_3$ preferably denotes H or methyl.

Examples of R, $R_1$, $R_4$, $R_5$, $R_6$, $R_7$ and $R_8$ as alkyl are methyl, ethyl and the isomers of propyl, butyl, pentyl, hexyl, heptyl, octyl, nonyl, decyl, undecyl and dodecyl.

$R_2$ preferably denotes H.

$R_1$ preferably denotes H, —CN, —OH, —$OC_1$–$C_6$-alkyl, —O—(O)C—$R_8$, —$OC_1$–$C_6$-hydroxyalkyl, —C(O)—$OR_4$ or —C(O)—$NR_5R_6$, or $R_1$ and $R_2$ together preferably denote —O—$C_1$–$C_6$-alkylidene—O—.

$R_1$ and $R_2$ together preferably signify —O—$C_1$–$C_8$— and most preferably —O—$C_1$–$C_4$-alkylidene—O—. A few examples of alkylidene are methylene, ethylidene, propylidene, butylidene, phenyl-methylidene, $(CH_3)_2C$= and $(CH_3)(C_6H_5)C$=.

$R_4$ preferably signifies $Li^+$, $Na^+$, $K^+$, $Mg^{2+}$, $Ca^{2+}$ or $C_1$–$C_6$-alkyl. For ammonium, the above-mentioned significances apply.

$R_5$ and $R_6$ independently of one another, preferably signify H, $C_1$–$C_4$-alkyl or $C_1$–$C_6$-hydroxyalkyl, $R_7$ preferably denotes H or methyl.

$R_8$ preferably represents $C_1$–$C_6$-alkyl, $C_1$- or $C_2$-halogenalkyl, cyclohexyl, benzyl or phenyl.

One preferred embodiment for the polymers to be used according to the invention with covalently bound receptors is those based on polyacryl- or polymethacryl-amides. These include those with the same or different recurring structural elements of formula IV or with the same or different recurring structural elements of formulae IV and V,

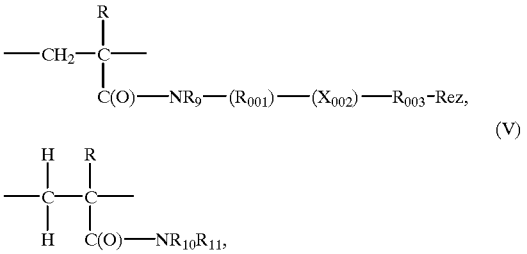

(IV)

(V)

wherein $X_{002}$ signifies —O—, —S—, —$NR_{002}$—, —C(O)—O—, —O—C(O)—, —O—C(O)—O—, —$SO_2$—O—, —O—$SO_2$—, —O—$SO_2$—O—, —$NR_{002}$—C(O)—, —C(O)—$NR_{002}$—, —$NR_{002}$—C(O)—O—, O—C(O)—$NR_{002}$—, $NR_{002}$—C(O)—$NR_{002}$—, —$NR_{002}$—$SO_{002}$—, —$SO_2$—$NR_{002}$—, —$NR_{002}SO_2$—O—, —O-$SO_2$—$NR_{002}$—, —$NR_{002}$—$SO_2$—$NR_{002}$—, —O—P(O)$OR_{12}$(O)—, —$NR_{002}$—P(O)—, $OR_{12}$(O)—, —O—P(O)$OR_{12}$—$NR_{002}$—, $NR_{002}$—P(O)$OR_{12}$—$NR_{002}$, —P(O)$OR_{12}$(O)— or —P(O)$OR_{12}$—$NR_{002}$—, $R_{001}$ represents a bivalent bridging group;

Rez denotes a monovalent radical of a receptor, $R_{002}$ denotes H, $C_1$–$C_{12}$-alkyl, $C_5$- or $C_6$-cycloalkyl, $C_5$- or $C_6$-cycloalkylmethyl or -ethyl, phenyl, benzyl or 1-phenyleth-2-yl;

$R_{003}$ signifies a direct bond, $C_1$–$C_{18}$-alkylene, $C_5$- or $C_6$-cycloalkylene, $C_6$–$C_{10}$-arylene or $C_7$–$C_{12}$-aralkylene;

R signifies H or methyl;

$R_9$ signifies H or $C_1$–$C_4$-alkyl;

$R_{12}$ denotes H, $C_1$–$C_{12}$-alkyl, ammonium, an alkali metal ion, for example $Li^+$, $Na^+$, and $K^+$, or an equivalent of an alkaline earth metal ion, for example $Mg^{2+}$ and $Ca^{2+}$; and $R_{10}$ and $R_{11}$ independently of one another, are H, $C_1$–$C_6$-alkyl or $C_1$–$C_6$-hydroxyalkyl, or $R_{10}$ and $R_{11}$ together are tetramethylene, pentamethylene, —$(CH_2)_2$—O—$(CH_2)_2$— or —$(CH_2)_2$—$NR_7$—$(CH_2)_2$—, whereby $R_7$ is H or $C_1$–$C_4$-alkyl.

For $R_{001}$, $X_{002}$, $R_{003}$, $R_{12}$ x, y and Rez, the above-mentioned preferred significances and amplifications are applicable.

$R_{003}$ preferably denotes a direct bond.

$R_9$ preferably signifies H, $R_{10 \text{ and } R11}$ preferably denote H, $C_1$–$C_4$-alkyl or $C_1$–$C_6$-hydroxyalkyl. Most preferably, $R_{10}$ and $R_{11}$ are each H.

The polyacryl- or polymethacryl-amides in question are most preferably those with recurring structural elements of formula IVa, or recurring structural elements of formulae IVa and Va,

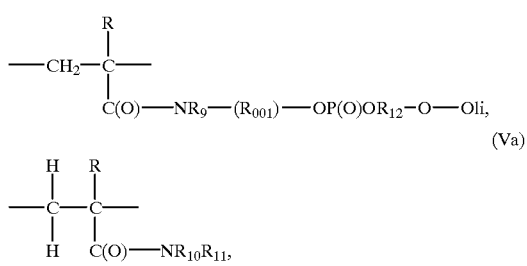

wherein

R signifies H or methyl and preferably H;

$R_9$ represents H or $C_1$–$C_4$-alkyl and preferably H;

$R_{001}$ denotes $C_1$–$C_{18}$-alkylene, or $C_2$–$C_{18}$-alkylene which is interrupted once or several times by —O—, —S—, —O—C(O)—, —C(O)—O—, —$NR_{002}$—C(O)—, —C(O)—$NR_{002}$—, —O—C(O)—O—, —O—C(O)—$NR_{002}$—, —$NR_{002}$—C(O)—O—, —$NR_{002}$—C(O)—, —O—P(O)$OR_{12}$(O)—, —$NR_{002}$—P(O)$OR_{12}$(O)—, —O—P(O)$OR_{12}$—$NR_{002}$—, —$NR_{002}$—P(O)$OR_{12}$—$NR_{002}$—, —$NR_{002}$—;

$R_{12}$ denotes H, $C_1$–$C_{12}$-alkyl, an alkali metal ion, for example $Li^+$, $Na^+$ and $K^+$, or an equivalent of an alkaline earth metal ion, for example $Mg^{2+}$ and $Ca^{2+}$;

$R_{10}$ and $R_{11}$ independently of one another, denote H or $C_1$–$C_4$-alkyl, preferably $R_{10}$ is H and $R_{11}$ is H or $C_1$–$C_4$-alkyl, and most preferably $R_{10}$ and $R_{11}$ each denote H; and Oli represents the monovalent radical of a receptor selected from the group of complementary oligonucleotides.

The oligonucleotides in question may be those from natural or synthetic nucleotides, or from both nucleotides. They may consist of 3 to 200, preferably 5 to 100, more preferably 5 to 50, and most preferably 8 to 30 nucleotide units.

The polymers to be used according to the invention are partly known or may be produced according to analogous or known processes. Basically, two methods may be employed: (1) The polymerisation of monomers from a receptor, to which a polymer-forming group is covalently bound directly or by a bridging group, either alone or together with comonomers, or (2) the reaction of soluble polymers containing functional groups with receptors containing appropriate functional groups. To produce the monomeric receptors with covalently bound receptor groups, the functional groups which are present and should not be reacted may be firstly protected with protecting groups. Afterwards, chain lengthening on a functional group may take place. Known methods for chain lengthening are for example etherification, esterification, amide formation, urea formation and urethane formation.

Linkage through functional groups may be carried out by generally known processes. Here, it is basically also possible to convert functional groups which are present into other functional groups, for example —$CH_2OH$— groups by oxidation to carboxylic acids, carboxylic acids to amides or halides, amine groups to isocyanate groups, alcohols or amines to carbonates or urethanes. Furthermore, it is possible to react alcohols or amines first of all with halogen-carboxylic acids (for example chloroacetic acid). Chain lengthening agents, for example epoxides, azirine, diols, diamines, dicarboxylic acids or esters and diisocyanates, may also be used once or several times in succession, thus precisely determining the length of the bridging group. These methods and processes for linking are known and are described in specialist literature. The comonomers and the starting compounds for production of the polymer-forming receptors are known, or partly available commercially, or may be produced by analogous processes.

The organic charged substances to be detected in the analytical mixture may have molecular weights of for example 300 to 1,000,000 or even more, preferably 300 to 500,000, more preferably 300 to 200,000, most preferably 300 to 100,000, especially 300 to 50,000.

It has also been found that for mixtures of electrically charged organic compounds with molecular weights preferably in the range of approximately at least 300 to approximately 1,000,000 da, polymer solutions of a certain viscosity, which can be filled and replaced, may advantageously be used as the separation phase, whereby the polymer contains covalently bound receptors. The solvent may be water, or aqueous buffers, either alone or in a mixture with organic solvents that are miscible with water. The reproducibility here (cycle time of the organic compounds) is surprisingly high, so that these stationary separation phases are suitable on the one hand for automation and on the other hand for standardisation of the qualitative determination of unknown mixtures of compounds. The resolution in many cases is even surprisingly so high that even mixtures of oligomeric compounds, which can only be distinguished in a building element or other structural element, may be separated and determined.

In a preferred embodiment of the process according to the invention, the replaceable separating agent used is a composition consisting of (a) 0.1 to 30% by weight of an essentially uncrosslinked water-soluble polymer, to which a receptor is covalently bound, and which has an average molecular weight of less than 5,000,000 daltons, and (b) 99.9 to 70% by weight of an aqueous buffer solution, either alone or together with an organic solvent which is miscible with water, whereby the composition has a viscosity of 20 to 600 mPas.

The molecular weight of the polymers in this composition is preferably 5000 to 5,000,000, more preferably 10,000 to 2,000,000, most preferably 10,000 to 1,000,000, and in particular 20,000 to 500,000. The higher the molecular weight, the more dilute the solutions which are suitably used.

If the average molecular weight of the polymer in these compositions is 10,000 to 500,000, and preferably 20,000 to 200,000 daltons, the compositions are new and are a further object of the invention.

The percentages by weight are always made up to one hundred percent. The molecular weight is determined by means of gel permeation chromatography using known standards of for example polyacrylamide of known molecular weight. The viscosity is determined on a rotation viscosimeter (Low Shear 30//MS 1/1) at 30° C.

For the polymers of the composition, the above-mentioned preferred significances and amplifications are applicable. Appropriate water-soluble polymers are known in large number. The choice of polymer and its molecular weight, as well as its concentration in the composition essentially determine the viscosity. The required molecular weight may be achieved either by means of a specific synthesis or by a for example hydrolytical degradation of higher molecular weight polymers. Certain molecular weights may similarly be set by using dialysis.

The amount of organic solvent may similarly be used to adjust the viscosity of the composition, and separating capacity will also be influenced. The composition preferably contains 1 to 80% by weight, more preferably 5 to 50% by weight, still more preferably 5 to 40% by weight, and most preferably 5 to 30% by weight of solvent, based on the buffer solution and the solvent. The solvents in question may be for example polar and protic or preferably aprotic solvents. A few examples are alkanols and polyols optionally substituted by methoxy or ethoxy, such as methanol, ethanol, propanol and butanol, methoxyethanol and ethoxyethanol; diols such as ethylene glycol, propanediol, butanediol, cyclohexanediol; triols such as glycerol or trimethylolpropane; and tetrols such as pentaerythritol; carboxylic acid amides and lactams, whose N-atoms may contain two or one methyl or ethyl substituent, such as formamide, acetamide, caprolactam, dimethylformamide, diethylacetamide and N-methylpyrrolidone, ketones and aldehydes such as acetaldehyde or acetone, sulphones such as dimethyl sulphone, diethyl sulphone and tetramethylene sulphone; sulphoxides such as dimethyl sulphoxide, diethyl sulphoxide and tetramethylene sulphoxide; and nitrites such as acetonitrile, propionitrile, butyronitrile and benzonitrile.

The composition contains 70 to 99.9% by weight, more preferably 75 to 99% by weight, still more preferably 80 to 99% by weight, and most preferably 90 to 99% by weight, of aqueous buffer solution. The aqueous buffer solution may have a pH value in the range 2 to 12, preferably 4 to 9.

The type, amount and concentration of buffer agent are selected so that the output of the capillary-electrophoretic system is up to about 10, preferably up to 3, most preferably 1 watt. Suitable buffer agents are for example those based on phosphates and borates, for example 10 to 500 mmols of TRIS [tris-(hydroxymethyl)-aminomethane] and 10 to 500 mmols of boric acid.

BIS [bis-(2-hydroxyethyl)amino-trishydroxymethylmethane] may also be employed or co-employed.

The viscosity of the composition is preferably 20 to 500, more preferably 50 to 500, most preferably 50 to 400 mPa·s.

The composition according to the invention is a clear and viscous solution and is eminently suitable for filling capillary tubes of electrophoretic apparatus, which can be removed again (rinsed out) after separation in order to refill the capillary tubes for further measurements. The apparatus is therefore re-useable which is a considerable economic advantage. This opens up the possibility of the commercial introduction of entire systems consisting of capillary tube and separating agents (so-called "kits"). A further quite considerable advantage is that separations of the invention according to charge, size and affinity may be combined in one capillary tube with separations only according to charge and size, using polymer gels or solutions without covalently bound receptors, and separating systems may be optimised, whereby when using replaceable separating phases, this may also take place fully automatically. The combination may be undertaken for example by mixing the separating systems (polymer gels or solutions). However, it is more convenient to use a spatially separated arrangement in the capillary tube, with replaceable separating phases.

A replaceable separating phase without covalently bound receptors is for example a composition consisting of (a) 0.1 to 30% by weight of an essentially uncrosslinked water-soluble polymer, which has an average molecular weight of less than 5,000,000, and (b) 99.9 to 70% by weight of an aqueous buffer solution either alone or in a mixture with at least one organic solvent which is miscible with water, whereby the composition has a viscosity of 20 to 600 mPa·s.

For this composition, the embodiments and preferences given above for the compositions as a replaceable separating agent with covalently bound receptors apply independently. The molecular weight is preferably 5000 to 5,000,000, more preferably 10,000 to 2,000,000, most preferably 10,000 to 1,000,000. The higher the molecular weight, the more dilute the solutions that are suitably employed. The average molecular weight of the polymer in these compositions is most preferably 10,000 to 500,000 and quite particularly 20,000 to 200,000 daltons.

The molecular weight is determined by means of gel permeation chromatography using known standards of for example polyacrylamide of known molecular weight. The viscosity is determined on a rotation viscosimeter (Low Shear 30//MS 1/1) at 30° C.

Suitable water-soluble polymers are known in large number. The choice of polymer and its molecular weight, as well as its concentration in the composition determine the viscosity. The required molecular weight may be achieved either by means of a specific synthesis or by a for example hydrolytical degradation of higher molecular weight polymers. The polymers must be stable under the chosen separation conditions. Both synthetic and natural polymers may be used. Examples are optionally partly etherified or esterified polyvinyl alcohols, polyvinyl pyrrolidone, optionally N-mono-alkylated or N-dialkylated polyacrylates or -methacrylates, polyethylene glycols or copolymers of ethylene glycol and 1,2-diols, for example 1,2-propylene glycol, polysaccharides or derivatives of polysaccharides, for example cellulose and cellulose-ether, starch, dextrans and carragenan. Dendrimers are also suitable as polymers.

Preferred water-soluble polymers are polyethylene glycols, polyacrylamides and polyvinyl alcohol.

The capillary tubes may be filled for example in the following manner:

1. Only with a polymer gel, whereby the same or different receptors are bound to the polymer, preferably no more than three different receptors.
2. (a) With a polymer gel, whereby the same receptors are bound to the polymer, (b) and subsequently with a polymer gel, whereby receptors that are different from or the same as (a) are bound to the polymer. In this embodiment, more than two, for example up to ten, more preferably up to five and most preferably up to three polymer gels may also be present in succession in the capillary tube, whereby different receptors are respectively bound to the different polymers.
3. (a) With a polymer gel, whereby the same or different receptors are bound to the polymer, and (b) subsequently with a polymer gel without bound receptors, for example one of the polymer solutions described above.
4. (a) With a polymer gel, whereby the same or different receptors are bound to the polymer, and (b) subsequently with a polymer gel without bound receptors, for example one of the polymer solutions described above, and (c) subsequently with a polymer gel, whereby receptors that are different from or the same as (a) are bound to the polymer.
5. (a) With a polymer gel without bound receptors, for example one of the polymer solutions described above, (b) subsequently with a polymer gel, whereby the same or different receptors are bound to the polymer, and (c) subsequently with a polymer gel which is the same as or different from (a), without bound receptors, for example one of the polymer solutions described above.

These embodiments already demonstrate that it is possible to have a large number of variants that are not mentioned, in order to adapt the system to specific separation problems.

The length of the individual separating phases in the capillary tube depends basically on the length of the capillary tube, the amount of bound receptors and the desired separating capacity for components in the analytical mixture.

A further object of the invention is a capillary tube for an electrophoretic separating apparatus, which is filled at least with one solid polymer gel, or a polymer solution having a viscosity of at least 20 mPa·s, with receptors covalently bound to the polymer, alone or in a combination with polymer gels or solutions without covalently bound receptors, whereby the average molecular weight of the polymer with covalently bound receptors is less than 2,000,000 and preferably less than 1,500,000 daltons; for example filled at least with a composition according to the invention and optionally with at least one of the above-described polymer solutions without covalently bound receptor.

Another object of the invention is a kit for an electrophoretic separating apparatus, consisting of (1) at least one container, in which there is a solid polymer gel, or a polymer solution having a viscosity of at least 20 mPa·s, with covalently bound receptors, whereby the polymer has an average molecular weight of up to 5,000,000 daltons, and (2) at least one container, in which there is a polymer solution or a polymer gel without receptors covalently bound to the polymer, as well as (3) optionally one or several capillary tubes for the capillary gel electrophoresis, whereby the capillary tubes may be filled with the gels or solutions; preferably consisting of at least (1) a container in which there is a composition according to the invention, and (2) at least one container in which there is a composition as described above without receptors covalently bound to a polymer, as well as (3) optionally one or several capillary tubes for the capillary gel electrophoresis.

A further object of the invention is a kit for an electrophoretic separating apparatus, consisting of (I) at least one container, in which there is a solid polymer gel, or a polymer solution having a viscosity of at least 20 mPa·s, with covalently bound receptors, whereby the average molecular weight of the polymer is less than 2,000,000 and preferably less than 1,500,000 daltons, and the capillary tubes may be filled with the gels and solutions; and (2) one or several capillary tubes for the capillary gel electrophoresis.

Capillary electrophoresis apparatus with detection devices (for example UV absorption measurement) are known, are described in specialist literature and available commercially from different manufacturers, for example the equipment P/ACE 5000 from the company Beckmann, Fullerton, Calif., USA, or $^{3D}CE$ from the company Hewlett Packard, Waldbronn, Germany. In order to avoid an electro-osmotic flow at the pH value of the stationary phase, the walls of the capillary tube are coated, for example with a thin layer of a polyvinyl alcohol. The layer may also be covalently bound by a linker.

The internal diameter of the capillary tubes may be for example 5 to 200, preferably 50 to 150 $\mu$m. The length of the capillary tube may be for example 0.1 to 200 cm, preferably 1 to 30 cm. It is expedient to apply a pressure, for example in the range of about $10^3$ to $10^7$ Pa when filling the capillary tubes with the composition to be used according to the invention.

The capillary tubes may consist of a material which is a non-conductor of electricity, for example glass, quartz or synthetic materials such as Teflon. Individual capillary tubes are frequently used with a protective layer for example of polyimide, so as to protect them from damage. Capillary tubes or capillary systems, which are obtainable by etching techniques, stamping or micro-milling on planar carriers, may also be used.

The capillary tube according to the invention for an electrophoretic separating apparatus is eminently suitable for separating electrically charged organic compounds, in particular bio-organic compounds, with molecular weights in the range of approximately at least 300 to 1,000,000 da, preferably 300 to 800,000 da, more preferably 300 to 500,000, and most preferably 300 to 200,000, quite particularly 300 to 100,000, and especially 300 to 50,000. The apparatus in this case may be re-used after one measurement by replacing the composition according to the invention in the capillary tube. To do this, the composition may be simply rinsed out under pressure, whereby water, organic solvents or mixtures of water and organic solvents may be used.

The organic compounds in question may be preferably natural or synthetic mixtures of compounds, for example oligonucleotides with up to about 5000 nucleotide units, oligomeric RNA or DNA sequences with up to about 5000 nucleotide units, oligomeric carbohydrates with up to 100 sugar units, and oligomeric peptides and proteins with up to 3000 amino acid units.

The process according to the invention may be carried out as follows in individual cases, whereby modifications for optimizing the separating capacity lie within the scope of the invention.

The electric field may be for example 50 to 2000, preferably 100 to 1500, most preferably 200 to 1200 and particularly 200 to 600 volts/cm.

Detection of the organic compounds is suitably undertaken using optical methods, for example using absorption measurement at a wave length normally in the UV range, or fluorescence detection such as a laser-induced fluorescence; or also mass-spectrometric or NMR-spectroscopic methods.

The concentration of organic compounds in the measuring sample (solution) may range from the minimolar, through the micromolar, picomolar to femtomolar.

The organic compounds may be dissolved in water, aqueous buffer solutions or mixtures of water or buffer solutions with organic solvents that are miscible with water. The capillary tube is charged by immersing one end into the measuring sample and applying a voltage for a short time (for example 1 to 10 seconds), whereby the organic compounds are taken up by electrophoresis. Charging may also be effected hydrodynamically, whereby a pressure difference is created between the ends of the capillary tube. The amount taken up may be for example from a few molecules through the attomolar to picomolar range.

It is a quite particular advantage in the case of electrokinetic charging that concentrations and preliminary purifications are made possible from very diluted solutions, for example extracts of natural substances, since complementary target analytical substances are bound to the receptors of the polymer gel and are not eluted. In this case, the electrokinetic charging procedure is understood to be a connecting stage for the separating process according to the invention. By carrying out the process in this way, the process according to the invention is even suitable as a preparatory method, with which sufficient quantities are made available for further examinations, and whereby other concentration processes such as the PCR method may be avoided. Electrokinetic charging is undertaken for this execution of the process under conditions at which the complementary target analytical substances bind to the receptors, for example at relatively low temperatures.

Separation is generally undertaken in the first stage of the process at a constant temperature, for example −20 to 90° C., preferably 10 to 50° C. In this first stage of the process, complementary analytical molecules are bound to the receptors and therefore not eluted. The unbound analytical molecules are eluted and can thus be separated and detected according to charge and size.

Elimination of the affinity of the bound complementary analytical molecules by altering the elution conditions may take place in various ways, for example by changing the electric field, changing the temperature (continuously, in stages or a one-off increase up to about 50° C.), changing the pH value (raising or lowering), adding denaturing agents such as bases (for example amines or urea), adding complementary organic compounds having a higher affinity for the receptor, or adding chaotropic reagents. These methods may also be combined.

Elution and detection of the compounds in the second stage of the process is generally undertaken as described for the first stage of the process. If two or several analytical compounds are bound, elution may be employed to separate according to size and charge.

The process according to the invention may be used in a large variety of fields in which a ligand/substrate system is important, especially in the analysis, detection and purification of mixtures of organic compounds which contain biologically active compounds. Examples which may be mentioned are:

Isolation of specific proteins and DNA molecules; purification of antibodies, antigens, oligonucleotides, DNA molecules and other active substances; analysis of oligonucleotides (antisense compounds) in complex mixtures, for example synthesis mixtures; separation and determination of antigens and analysis of reactivity with antibodies; testing processes (screening) to detect for example enzyme inhibitors in libraries of compounds and in biological extracts; testing processes (screening) to detect complementary DNA molecules in DNA libraries; analysis processes (screening tool) to map organisms such as plants, animals and micro-organisms; diagnostic processes to determine diseases by means of body-specific peptides, or by means of gene samples; processes in the form of immuno- and enzyme-assays; processes for the selective isolation of DNA molecules; processes for the selective isolation of allelic genes from mixtures of c-DNA or genomic libraries with respect to cloning.

The process according to the invention offers many, in part surprising, advantages. Higher resolution and selectivity is attained, especially in the case of complex biological analytical mixtures, which may be present in small concentrations and large volumes. In addition, systems may be offered with receptors based on consumers. The process may be simply operated in a fully automatic manner using standard appliances. The process also has high sensitivity, even with small amounts of samples. This is a particularly simple analysis process, in which results may be obtained at short intervals of time. Polymers with more than one covalently bound receptor or mixtures of polymer gels with different covalently bound receptors may be used simultaneously. Through having the most varied modifications, the analysis process offers high flexibility and possibilities of optimising certain problems. Furthermore, it is possible to carry out parallel separation and detection of the same or different analytical substances. It is particularly advantageous that the system can be used to solve several very different problems in the separation and detection of biologically active substances, even as far as diagnostics. The reagents required are readily accessible and the polymer gels may be synthesized specifically in accordance with simple standard methods.

A further object of the invention is the usage of the process according to the invention for the isolation of specific proteins and DNA molecules; the purification of antibodies, antigens, oligonucleotides, DNA molecules and other active substances; the analysis of oligonucleotides in complex mixtures; the separation and determination of antigens and analysis of reactivity with antibodies; as testing processes to detect enzyme inhibitors in compound libraries and in biological extracts; as testing processes to detect complementary DNA molecules in DNA libraries; as analysis processes to map organisms from the group plants, animals and micro-organisms; as diagnostic processes to determine diseases by means of body-specific peptides, or by means of gene samples; as immuno- and enzyme-assays; as processes for the selective isolation of DNA molecules; as processes for the selective isolation of allelic genes from mixtures of c-DNA or genomic libraries.

Another object of the invention is the use of compositions (A) consisting of (a) 0.1 to 30% by weight of an essentially uncrosslinked water-soluble polymer, to which a receptor is covalently bound, and which has an average molecular weight of less than 5,000,000 and (b) 99.9 to 70% by weight of an aqueous buffer solution, either alone or together with an organic solvent which is miscible with water, whereby the composition has a viscosity of 20 to 600 mPa·s, either alone or together with a composition (B) arranged in a capillary tube before or after composition (A), composition (B) consisting of (a) 0.1 to 30% by weight of an essentially uncrosslinked water-soluble polymer which has an average molecular weight of less than 5,000,000 and (b) 99.9 to 70% by weight of an aqueous buffer solution, either alone or mixed with at least one organic solvent which is miscible with water, whereby the composition has a viscosity of 20 to 600 mPa·s, as separating agents in capillary affinity gel electrophoresis of at least two-stages.

The following examples illustrate the invention.

The x axis indicates time and the y axis indicates the absorption at 260 nm. In addition, the temperatures at separation (elution) are indicated through the x axis (dotted line).

A) Production of Starting Compounds

EXAMPLE A1

Production of

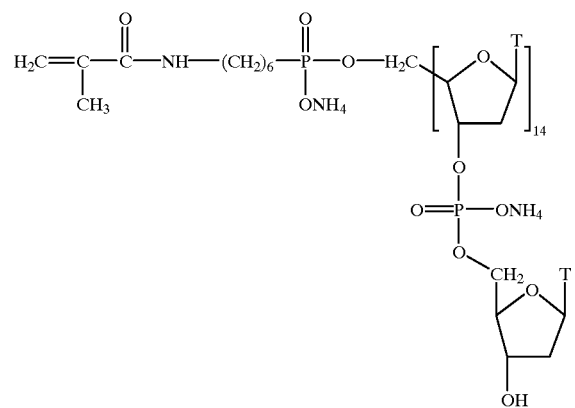

wherein T signifies

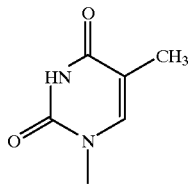

a) The oligonucleotide is produced according to standard protocol by the β-cyanoethyl-phosphoramidit method in an automated DNA synthesizer ABI 394 B. In the last stage, by the same method, monomethoxytrityl-NH—(CH$_2$)$_6$—OP[β-cyanoethyl][N(i-propyl)$_2$] is bound to the terminal CH$_2$OH-group of the oligonucleotide.

b) The synthesis column with the carrier material, to which the aminohexamethyl oligonucleotide (50 mg, about 1 mmol) is bound, is removed from the synthesizer, the carrier material dried by drawing off in a vacuum and then washed with dichloromethane. Then, a solution of 0.25 mmols of methacrylic acid anhydride and 0.25 mmols of N-methylmorpholine in 1 ml of dichloromethane is added to the column and left to react for 30 minutes at room temperature. Afterwards, the column is washed with dichloromethane and acetonitrile and dried by drawing off in a vacuum. The carrier material is placed in a flask, 1 ml of concentrated aqueous ammonium hydroxide is added and left to stand over night at 55° C. The supernatant liquid is quickly evaporated to remove the excess ammonia and the solution obtained is chromatographed to remove small molecules. The salt-free solution obtained is lyophilised without heating and then used directly for the polymerisation.

EXAMPLE A2

Production of

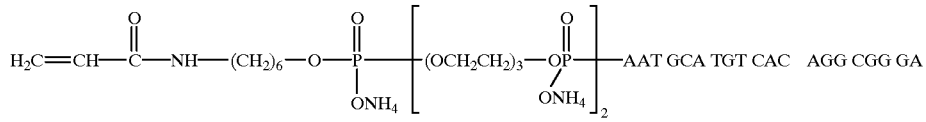

a) The oligonucleotide with the bridging group H[(OCH$_2$CH$_2$)$_3$OP(O)—ONa]$_2$— (by means of dimethoxytritylO—[(CH$_2$CH$_2$O)$_3$]$_2$OP[β-cyanoethyl][N(i-propyl)$_2$]) is produced according to standard protocol by the β-cyanoethylphosphoramidit method in an automated DNA synthesizer ABI 394 B. In the last stage, by the same method, monomethoxytrityl-NH—(CH$_2$)$_6$—OP[βcyanoethyl][N(i-propyl)$_2$] is bound to the terminal CH$_2$OH-group of the bridging group.

b) The process is as in example A1, part b), but using acrylic acid anhydride.

B) Production of Polymers

EXAMPLE B1

2477 μl of a three percent solution of acrylamide in aqueous buffer (100 mmols TRIS, 100 mmols boric acid) are degassed using helium in a flask. Then, 7.5 μl of monomer (0.1 mg monomer per μl) according to A1, 8 μl of a ten percent (weight/volume) solution of ammonium persulphate and 8 μl of a ten percent (volume/volume) solution of tetramethylethylenediamine, each in water, are added. The flask is sealed, shaken and undergoes an ultrasonic bath for 5 minutes. It is then left to react for 30 minutes at room temperature, and the reaction mixture is placed in dialysis equipment to remove oligomers with a molecular weight of less than 10,000 daltons. The solution is dialysed for 48 hours against 1 liter of water, whereby the water is replaced three times. Afterwards, the polymer solution is placed in a Falcon flask, cooled with dry ice/acetone and lyophilised. The yield is about 75%. The weight ratio of acrylamide to monomer according to example A1 is 100:1.

EXAMPLE B2

The process is as in example B1, but using the monomer according to example A2. The yield is about 75%. The weight ratio of acrylamide to monomer according to example A2 is 100:1.

C) Production of Polymer Gels as Separating Agents

EXAMPLE C1

The polymer according to example B1 is dissolved in an aqueous buffer consisting of 100 mmols of TRIS [(trihydroxymethyl)aminomethane] and 100 ml of boric acid (pH 8.3) to make a 1.5% solution, and centrifuged to remove undissolved parts. The solution which is ready for use may be stored until it is used. The viscosity is about 40 mPa·s.

EXAMPLE C2

The process is as in example C1, but using the polymer of example B2, whereby the buffer consists of 58 mmols TRIS, 58 mmols boric acid, 24% by volume dimethylformamide, 20% by volume dimethyl sulphoxide and the remainder water. The viscosity is about 100 mPa·s.

D) Application Examples

EXAMPLE D1

496 μl of a three percent solution of acrylamide in aqueous buffer (100 mmols TRIS, 100 mmols boric acid) are degassed using helium in a flask. Then, 1.5 μl of monomer (0.1 mg monomer per μl) according to example A1, 1.3 μl of a ten percent (weight/volume) solution of ammonium persulphate and 1.3 μl of a ten percent (volume/volume) solution of tetramethylethylenediamine, each in water, are added. The polymer solution is filled using a syringe into a capillary tube of "fused silica" which is silylated with methacrylic acid-3-trimethoxysilyl-propyl-ester. Polymerisation takes place for 24 hours, after which it is equilibrated with aqueous buffer. The capillary tube has a length of 24 cm and an inside diameter of 77 μm and at 17 cm has a UV-transmitting window. An aqueous solution containing 100 mmols of TRIS [(trihydroxymethyl)aminomethane] and 100 mmols of boric acid (pH 8.3) is used as the electrophoresis buffer. The capillary tube is equilibrated at −5 kV for 10 minutes. Afterwards, stable UV basic absorption and a stable current are observed. Then, the filled capillary tube is charged electrokinetically at −6 kV for 5 seconds and at 16° C. with one sample dC$_{12-18}$ (0.0005 OD/μl) and one sample dA$_{15}$ (0.0005 OD/μl). Afterwards, a voltage of −5 kV is applied, and elution effected at 16° C. After about 7.1 minutes, $dC_{12-18}$ is eluted whilst splitting open. After 10 minutes, the $dA_{15}$ is still not observed. The temperature is raised to 40° C. and elution continued. About 3.8 minutes after raising the temperature, a sharp absorption is observed, which corresponds to the eluted $dA_{15}$.

EXAMPLE D2

This example demonstrates the capacity of the method for the separation of $dA_{15}$ with the simultaneous splitting open of mismatched structures.

The polymer solution according to C1 is filled into a capillary tube (CElect N, manufacturer Supelco) under a pressure of $3.5 \cdot 10^5$ Pa over 10 minutes. The capillary tube has a length of 24 cm and an inside diameter of 75 µm and at 17 cm has a UV-transmitting window. An aqueous solution consisting of 100 mmols of TRIS and 100 mmols of boric acid (pH 8.3) is used as the electrophoresis buffer. The capillary tube is equilibrated at –5 kV for 10 minutes, whereby an additional 0.5 mmols of $MgCl_2$ are present in the inlet and outlet container. Afterwards, stable UV basic absorption and a stable current are observed. Then, the filled capillary tube is charged electrokinetically at –6 kV for 6 seconds and at 23° C. with one sample $dA_{15}$ (0.0005OD/µl). Then, a mixture of $d(TA_6TA_6T)$, $d(A_7TA_6T)$ and $d(A_7TA_7)$ is injected electrokinetically at –8 kV for 9 seconds. Afterwards, a voltage of –5 kV is applied, and elution effected at a temperature of 23° C. After 6.5 minutes, the temperature is raised to 29° C. After about 7.7 minutes, $d(TA_6TA_6T)$ is eluted, after about 9.7 minutes $d(A_7TA_6T)$, and after 10.5 minutes $d(A_7TA_7)$. After 13 minutes, the temperature is raised to 50° C. Only after a total of 17.7 minutes is $dA_{15}$ eluted.

EXAMPLE D3

The polymer solution according to example C2 is filled into a capillary tube (CElect N, manufacturer Supelco) under a pressure of $3.5 \cdot 10^5$ Pa over 10 minutes. The capillary tube has a length of 24 cm and an inside diameter of 75 µm and at 17 cm has a UV-transmitting window. 70 mmols of TRIS and 70 mmols of boric acid (pH 8.3) in 70 percent water (volume/volume) and 30 percent dimethylformamide (volume/volume) are used as the electrophoresis buffer. The capillary tube is equilibrated at –25 kV for 12 minutes. Afterwards, stable UV basic absorption and a stable current are observed. Then, the filled capillary tube is charged electrokinetically at –4 kV for 10 seconds and at 13° C. with a mixture of $dT_{10}$ (0.0005 OD/µL), $dT_{15}$ (0.0005 OD/µL) and $dT_{20}$ (0.0005 OD/µL). Then, 5'-TCC CGC CTG TGA CAT GCA TT-3' (0.001 OD/µL) is electrokinetically charged at –10 kV for 20 seconds. After this, a voltage of –15 kV is applied and elution effected at a temperature of 13° C. After about 9.1 minutes, $dT_{10}$ is elated, after about 9.6 minutes $dT_{15}$, and after 10.4 minutes $dT_{20}$. After about 13 minutes, the temperature is raised to 50° C. After a total of 17.2 minutes, the heteromer is eluted.

What is claimed is:

1. Process for the selective separation of electrically charged target molecules in an analytical mixture by means of capillary affinity gel electrophoresis, using a capillary tube which is at least partly filed with a polymer gel, which is solid, or a solution of the polymer in a solvent, having a viscosity of at least 20 mPa's, whereby receptors for target molecules are covalently bound to the polymer, and an electric filed of at least 50 volts/cm is applied, and wherein the process comprises (a) charging the capillary tube with the analytical mixture whereby the target molecules are bound to the receptors, (b) in a first stage, eluting remaining components of said analytical mixture under a first set of eluting conditions; (c) in a second stage, changing the eluting conditions to release said target molecules and eluting said target molecules, and (d) detecting said target molecules characterized in that the polymer comprises a copolymer containing structural elements with covalently bound receptors in a quantity of 0.01 to 99.9% by weight.

2. Process for the selective separation of electrically charged target molecules in an analytical mixture by means of capillary affinity gel electrophoresis, using a capillary tube which is at least partly filed with a polymer gel, which is solid, or a solution of the polymer in a solvent, having a viscosity of at least 20 mPa's, whereby monovalent receptor radicals for target molecules are covalently bound to the polymer directly or through a linkage, and an electric field of at least 50 volts/cm is applied, and wherein the process comprises (a) charging the capillary tube with the analytical mixture, whereby the target molecules are bound to the receptors, (b) in a first stage eluting remaining components of said analytical mixture under a first set of eluting conditions; (c) in a second stage changing the eluting conditions to release said target molecules and eluting said target molecules, and (d) detecting said target molecules characterized in that the monovalent radical receptor bound to the polymer corresponds to formula I

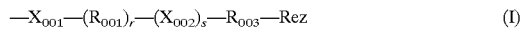

$$-X_{001}-(R_{001})_r-(X_{002})_s-R_{003}-Rez \qquad (I)$$

wherein $X_{001}$ signifies a direct bond or $X_{002}$ and $X_{001}$ independently of one another signify —O—, —S—, —$NR_{002}$—, —C(O)—O—, —O—C(O)—, —O—C(O)—, —$SO_2$—O—, O—$SO_2$—, O—$SO_2$—O—, —$NR_{002}$—C(O)—, —C(O)—$NR_{002}$—, —$NR_{002}$—C(O)—O—, O—C(O)—$NR_{002}$, —$NR_{002}$—C(O)—$NR_{002}$, —$NR_{002}$—$SO_2$—, —$SO_2$—$NR_{002}$, —$NR_{002}$—$SO_2$—O—, —O—$SO_2$—$NR_{002}$, —$NR_{002}$—$SO_2$—$NR_{002}$—, —O—P(O)$OR_{12}$(O)—, —$NR_{002}$—P(O)$R_{12}$(O)—, —O—P(O)$OR_{12}$—$NR_{002}$—, —$NR_{002}$—P(O)$OR_{12}$—$NR_{002}$—, P(O)$OR_{12}$—O—, —P(O)$OR_{12}$—$NR_{002}$—, $R_{001}$ links $X_{001}$ with $X_{002}$ when s is 1 and when $R_{003}$ when s is 0, Rez denotes a monovalent radical of a receptor, $R_{002}$ signifies H, $C_1$–$C_{12}$-alkyl, $C_5$- or $C_6$-cycloalkyl, $C_5$- or $C_6$-cycloalkylmethyl or -ethyl, phenyl, benzyl, or 1-phenyleth-2-yl, $R_{003}$ signifies a direct bond, $C_1$–$C_{18}$ alkylene, $C_5$- or $C_6$-cycloalkylene, $C_6$–$C_{10}$-arylene or $C_7$–$C_{12}$-aralkylene, $R_{12}$ denotes H, $C_1$–$C_{12}$-alkyl, ammonium, an alkali metal ion or an equivalent of an alkaline earth metal thereof, R signifies the numbers 0 or 1 and s signifies the number 0 or 1 and s is 0 when r is 0.

3. Process for the selective separation of electrically charged target molecules in an analytical mixture by means of capillary affinity gel electrophoresis, using a capillary tube which is at least partly filed with a polymer gel, which is solid, or a solution of the polymer in a solvent, having a viscosity of at least 20 mPa's, whereby receptors for target molecules are covalently bound to the polymer, and an electric filed of at least 50 volts/cm is applied, and wherein the process comprises (a) charging the capillary tube with the analytical mixture whereby the target molecules are, bound to the receptors, (b) in a first stage eluting remaining components of said analytical mixture under a first set of eluting conditions; (c) in a second stage changing the eluting conditions to release said target molecules and eluting said target molecules, and (d) detecting said target molecules characterized in that the polymers used contain the same or different recurring structural elements of formula I, or the same or different structural elements of formulae II and III, $R_{12}$ denotes H, $C_1$–$C_{12}$-alkyl, ammonium, an alkali metal ion or an equivalent of an alkaline earth metal thereof, r signifies the numbers 0 or 1 and s signifies the number 0 or 1 an

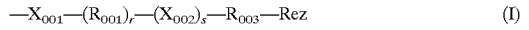  (I)

wherein $X_{001}$ signifies a direct bond or $X_{002}$ and $X_{001}$ independently of one another signify —O—, —S—, —$NR_{002}$—, —C(O)—O—, —O—C(O)—, —O—C(O)—, —$SO_2$—O—, O—$SO_2$—, O—$SO_2$—O—, —$NR_{002}$—C(O)—, —C(O)—$NR_{002}$—, —$NR_{002}$—C(O)—O—, —O—C(O)—$NR_{002}$, —$NR_{002}$—C(O)—$NR_{002}$—, —$NR_{0002}$ —$SO_2$—, —$SO_2$—$NR_2$, —$NR_{002}$—$SO_2$—O—, —O—$SO_2$—$NR_{002}$, —$NR_{002}$—$SO_2$—$NR_{002}$—, —O—P(O)$OR_{12}$(O)—, —$NR_{002}$—P(O)$R_{12}$(O)—, —O—P(O)$OR_{12}$—$NR_{002}$—, —$NR_{002}$—P(O) $OR_{12}$—$NR_{002}$—, —P(O)$OR_{12}$—O—, —P(O)$OR_{12}$—$NR_{002}$—, $R_{001}$ links $X_{001}$ with $X_{002}$ when s is 1 and with $R_{003}$ when s is 0, Rez denotes a monovalent radical of a receptor, $R_{002}$ signifies H, $C_1$–$C_{12}$-alkyl, $C_5$- or $C_6$-cycloalkyl, $C_5$- or $C_6$-cycloalkylmethyl or -ethyl, phenyl, benzyl, or 1-phenyleth-2-yl, $R_{003}$ signifies a direct bond, $C_1$–$C_{18}$ alkylene, $C_5$- or $C_6$-cycloalkylene, $C_6$-$C_{10}$-arylene or $C_7$–$C_{12}$-aralkylene, d s is 0 when r is 0,

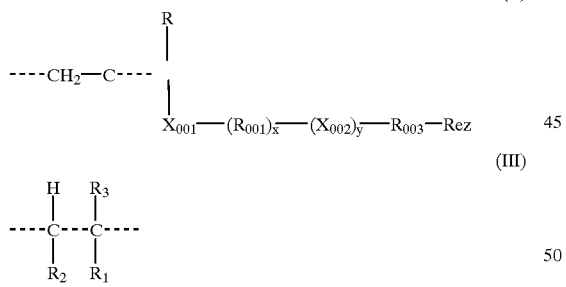

wherein $X_{001}$ $R_{001}$, $X_{002}$, $R_{003}$ and Rez have the significances given above for formula I;

R denotes H or $C_1$–$C_4$-alkyl;

$R_3$ signifies H, $C_1$–$C_{10}$-alkyl, phenyl or $C_1$–$C_4$-alkylphenyl;

$R_2$ represents H, —C(O)—$OR_4$ or —C(O)—$NR_5R_6$;

$R_1$ represents H, Cl, —CN, —OH, $OC_1$–$C_6$-alkyl, O(O)C—$R_8$, —$OC_1$–$C_6$-hydroxyalkyl, phenyl, $C_1$–$C_4$-alkylphenyl, —C(O)-$OR_4$, or —C(O)—$NR_5R_6$, or $R_1$ and $R_2$ taken together signify —O—$C_1$–$C_{12}$-alkylidene-O—;

$R_4$ signifies H, ammonium, an alkali metal ion, an alkaline earth metal ion equivalent, $C_1$–$C_{12}$-alkyl, phenyl or

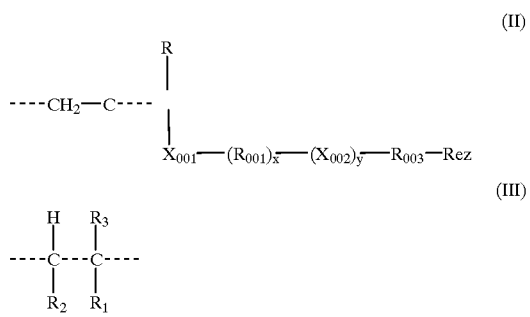

phenyl;

$R_5$ and $R_6$, independently of one another, denote H, $C_1$–$C_{12}$-alkyl, $C_1$–$C_8$hydroxyalkyl, cyclohexyl, benzyl or phenyl, or $R_5$ and $R_6$ denote tetra-or pentamethylene, —$(CH_2)_2$—O—$(CH_2)_2$— or —$(CH_2)_2$—$NR_7$—$(CH_2)_2$—, whereby $R_7$ is H or $C_1$–$C_4$-alkyl, x and y each denote 0 or 1 and x+y are 1 or 2; and $R_8$ signifies $C_1$–$C_{12}$-alkyl, $C_1$–$C_4$-halogenoalkyl, $C_5$- or $C_6$-cycloalkyl, benzyl or phenyl.

4. Process for the selective separation of electrically charged target molecules in an analytical mixture by means of capillary affinity gel electrophoresis, using a capillary tube which is at least partly filed with a polymer gel, which is solid, or a solution of the polymer in a solvent, having a viscosity of at least 20 mPa's, whereby receptors for target molecules are covalently bound to the polymer, and an electric filed of at least 50 volts/cm is applied, and wherein the process comprises (a) charging the capillary tube with the analytical mixture whereby the target molecules are, bound to the receptors, (b) in a first stage eluting remaining components of said analytical mixture under a first set of eluting conditions; (c) in a second stage changing the eluting conditions to release said target molecules and eluting said target molecules, and (d) detecting said target molecules characterised in that the used polymers are polyacryl- or polymethacryl-amides with recurring structural elements of formulae IVa and Va,

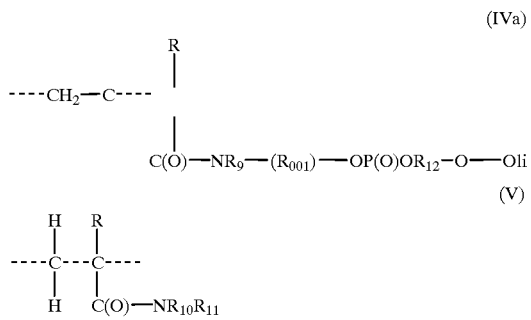

wherein

R signifies H or methyl;

$R_9$ represents H or $NR_{002}$;

$R_{001}$ denotes $C_1$–$C_{18}$-alkylene, or $C_2$–$C_{18}$-alkylene which is interrupted once or several times by —O—, S—, O—C(O)—, —$NR_{002}$—C(O)—, —C(O)—$NR_{002}$—, —O—C(O)—O—, —O—C(O)—$NR_{002}$—, —$NR_{002}$—C(O)—O—, —$NR_{002}$—C(O)—, —O—P(O)$OR_{12}$(O)—, —$NR_{002}$—P(O)$OR_{12}$(O)—, —O—P(O)$OR_{12}$—$NR_{002}$—, —$NR_{002}$—P(O)$OR_{12}$—$NR_{002}$—, —$NR_{002}$—;

$R_{002}$ signifies H, $C_1$–$C_{12}$-alkyl, $C_5$- or $C_6$-cycloalkyl, $C_5$- or $C_6$-cycloalkylmethyl or -ethyl, phenyl, benzyl or 1-pheneth-2-yl;

$R_{12}$ denotes H, ammonium, $C_1$–$C_{12}$-alkyl, an alkali metal ion or an alkaline earth metal ion equivalent;

$R_{10}$ and $R_{11}$ independently of one another, denote H or $C_1$–$C_4$-alkyl; and Oli represents an oligonucleotide.

5. Process for the selective separation of electrically charged target molecules in an analytical mixture by means of capillary affinity gel electrophoresis, using a capillary tube which is at least partly filed with a polymer gel, which is solid, or a solution of the polymer in a solvent, having a viscosity of at least 20 mPa's, whereby receptors for target molecules are covalently bound to the polymer, and an electric filed of at least 50 volts/cm is applied, and wherein the process comprises (a) charging the capillary tube with the analytical mixture whereby the target molecules are, bound to the receptors, (b) in a first stage eluting remaining components of said analytical mixture under a first set of eluting conditions; (c) in a second stage changing the eluting conditions to release said target molecules and eluting said target molecules, and (d) detecting said target molecules characterised in that the capillary tube is filled with a composition consisting of (a) 0.1 to 30% by weight of an essentially uncrosslinked water-soluble polymer, to which a receptor is covalently bound, and which has an average molecular weight of less than 5,000,000, and (b) 99.9 to 70% by weight of an aqueous buffer solution, either alone or together with an organic solvent which is miscible with water, whereby the composition has a viscosity of 20 to 600 mPa's.

6. Process for the selective separation of electrically charged target molecules in an analytical mixture by means of capillary affinity gel electrophoresis, using a capillary tube which is at least partly filed with a polymer gel, which is solid, or a solution of the polymer in a solvent, having a viscosity of at least 20 mPa's, whereby receptors for target molecules are covalently bound to the polymer, and an electric filed of at least 50 volts/cm is applied, and wherein the process comprises (a) charging the capillary tube with the analytical mixture whereby the target molecules are, bound to the receptors, (b) in a first stage eluting remaining components of said analytical mixture under a first set of eluting conditions; (c) in a second stage changing the eluting conditions to release said target molecules and eluting said target molecules, and (d) detecting said target molecules characterised in that the polymer gel is replaceable and is a composition consisting of (a) 0.1 to 30% by weight of an essentially uncrosslinked water-soluble polymer to which a receptor is covalently bound, which has an average molecular weight of less than 5,000,000 daltons, and (b) 99.9 to 70%: by weight of an aqueous buffer solution either alone or together with at least one organic solvent which is miscible with water, whereby the composition has a viscosity of 20 to 600 mPa's.

7. Process for the selective separation of electrically charged target molecules in an analytical mixture by means of capillary affinity gel electrophoresis, using a capillary tube which is at least partly filed with a polymer gel, which is solid, or a solution of the polymer in a solvent, having a viscosity of at least 20 mPa's, whereby receptors for target molecules are covalently bound to the polymer, and an electric filed of at least 50 volts/cm is applied, and wherein the process comprises (a) charging the capillary tube with the analytical mixture whereby the target molecules are, bound to the receptors, (b) in a first stage eluting remaining components of said analytical mixture under a first set of eluting conditions; (c) in a second stage changing the eluting conditions to release said target molecules and eluting said target molecules, and (d) detecting said target molecules characterized in that the elution conditions are changed in stages.

* * * * *